United States Patent
Enns et al.

(10) Patent No.: US 7,842,217 B2
(45) Date of Patent: Nov. 30, 2010

(54) ENTERAL-ONLY SYRINGE AND METHOD OF MANUFACTURING SAME

(75) Inventors: Thomas Frederick Enns, Mississauga (CA); Adnan Stetieh, Mississauga (CA)

(73) Assignee: Benlan, Inc., Oakville, Ontario (CA)

( * ) Notice: Subject to any disclaimer, the term of this patent is extended or adjusted under 35 U.S.C. 154(b) by 130 days.

(21) Appl. No.: 11/692,703

(22) Filed: Mar. 28, 2007

(65) Prior Publication Data

US 2008/0243104 A1 Oct. 2, 2008

(51) Int. Cl.
*B29C 45/14* (2006.01)

(52) U.S. Cl. .................. 264/259; 264/247; 264/241; 264/250; 264/251; 264/255; 264/260; 264/263; 264/279; 264/270; 264/271.1; 264/272.5; 264/275; 264/277; 264/279.1; 264/297.2; 264/299; 264/280; 264/328.1; 264/328.14; 264/334; 604/240; 604/264; 604/270; 604/523; 604/533

(58) Field of Classification Search .............. 264/271.1, 264/272.5, 297.2, 259, 250, 251, 255, 241, 264/260, 263, 275, 277, 279.1, 279, 297.1, 264/247, 299, 328.1, 328.14, 334, 280; 604/240, 604/264, 270, 523, 533
See application file for complete search history.

(56) References Cited

U.S. PATENT DOCUMENTS

2003/0014005 A1* 1/2003 Chiba et al. .................. 604/38
2008/0065023 A1* 3/2008 Kennard ..................... 604/187

\* cited by examiner

*Primary Examiner*—Jeffrey Wollschlager
*Assistant Examiner*—Stella Yi

(74) *Attorney, Agent, or Firm*—William J. Sapone; Coleman Sudol Sapone P.C.

(57) ABSTRACT

A method of manufacturing a syringe for use in enteral feeding includes providing a premolded syringe body having a plunger end and an outlet end, loading the premolded syringe body into a mold having a core pin extending into the outlet end of the premolded syringe body, closing the mold to thereby retain the premolded syringe therein and to close a mold cavity around the outlet end of the syringe body, injection molding by injecting plastic molding material into the mold cavity and cooling to thereby form a tip at the outlet end of the premolded syringe body, and opening the mold and extracting the syringe body and the tip.

5 Claims, 5 Drawing Sheets

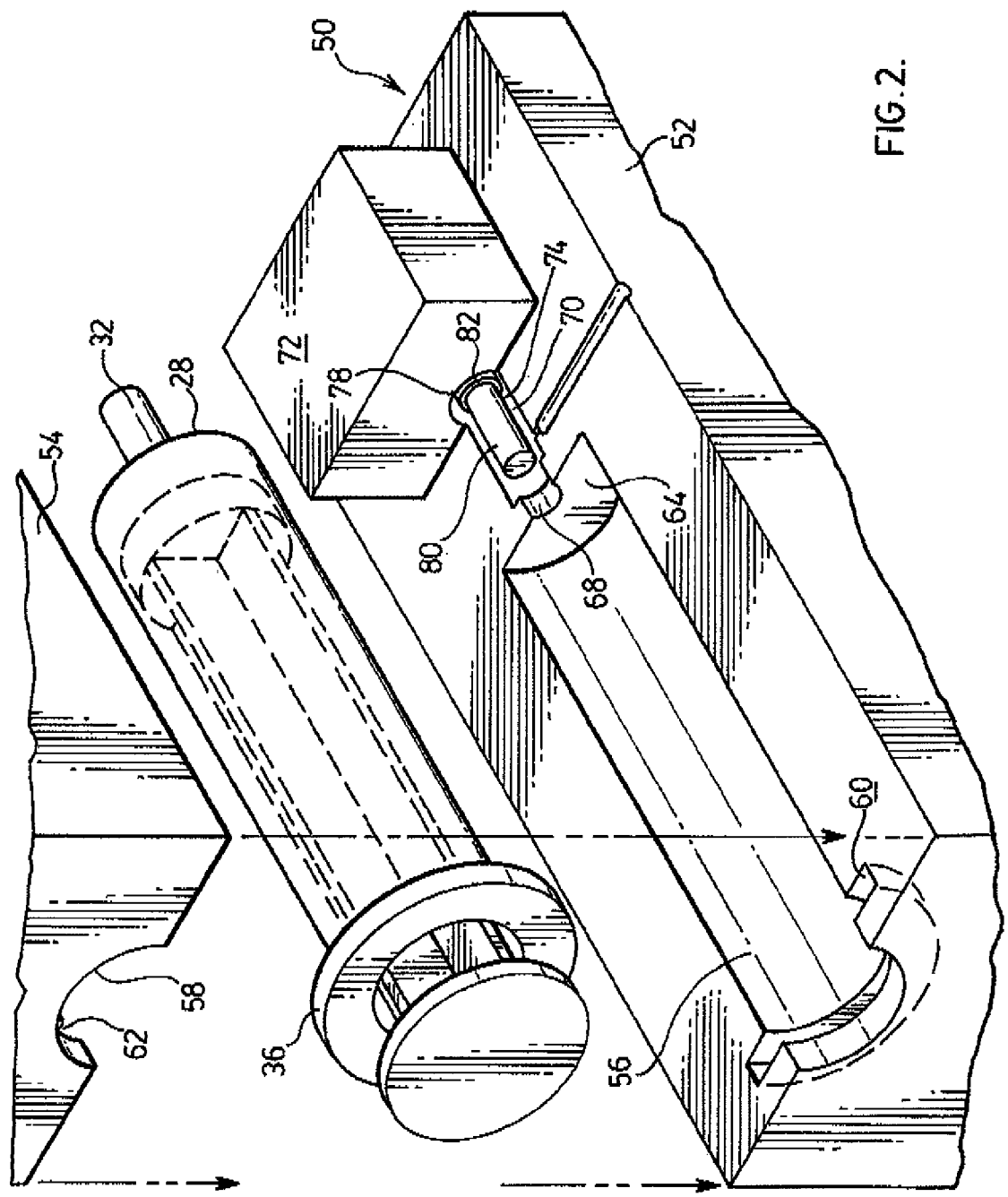

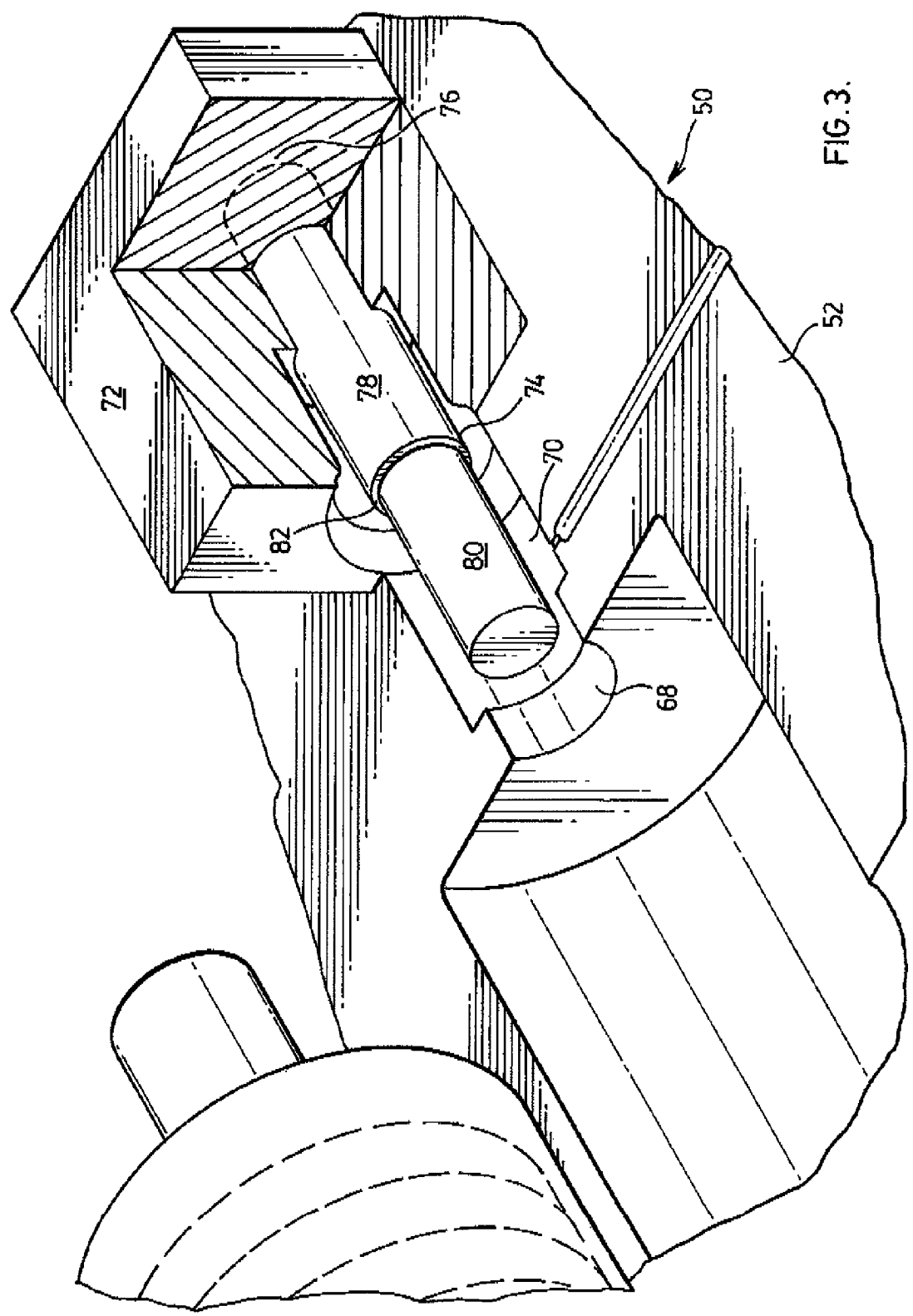

ENTERAL-ONLY SYRINGE AND METHOD OF MANUFACTURING SAME

FIELD OF THE INVENTION

The present invention relates to enteral feeding syringes for use with enteral feeding tubes and feeding sets for the delivery of food or medication to a patient.

BACKGROUND OF THE INVENTION

Enteral tube feeding is known for feeding patients such as infants or children who are unable to ingest foods orally. The enteral tube is inserted either orally or nasally, through the oesophagus and into the stomach and is used to deliver nutritive liquid feed to the stomach of the infant or child for digestion. One end of the tube remains external to the patient and is used for connecting an enteral feeding syringe for delivery of the liquid feed. The opposing end of the tube is located in the stomach of the patient to which the liquid feed is delivered.

A variety of enteral feeding tubes including polyurethane and silicone tubes are used for more than a single delivery of liquid feed to the patient to avoid problems associated with frequent insertion and extraction of feeding tubes. For example, polyurethane feeding tubes are generally used for up to about 30 days while silicone feeding tubes can be used even longer.

A connector at the end of the feeding tube that is external to the patient is used for connecting the enteral feeding syringe to the feeding tube. Alternatively, a connector at the end of an enteral feeding extension set is used for connecting the enteral feeding tube to an enteral feeding syringe.

Improvements in enteral feeding syringes are driven by the desire for increased safety, usability and improved performance.

SUMMARY OF THE INVENTION

According to one aspect, there is provided a method of manufacturing a syringe for use in enteral feeding includes providing a premolded syringe body having a plunger end and an outlet end, loading the premolded syringe body into a mold having a core pin extending into the outlet end of the premolded syringe body, closing the mold to thereby retain the premolded syringe therein and to close a mold cavity around the outlet end of the syringe body, injection molding by injecting plastic molding material into the mold cavity and cooling to thereby form a tip at the outlet end of the premolded syringe body, and opening the mold and extracting the syringe body and the tip.

According to another aspect, there is provided a syringe for use in enteral feeding. The syringe includes a syringe body having a plunger end and an outlet end, an enteral tip overmolded on the outlet end of the syringe body and sized for insertion into an enteral connector, and a plunger for insertion into the syringe body for delivery of fluid feed from the syringe body and through the enteral tip.

According to another aspect, there is provided a mold for injection molding a syringe body for use in enteral feeding. The mold includes a first side having a slot for receiving a premolded syringe body that has a plunger end and an outlet end, and a core pin for extending into the outlet end of the premolded syringe body. The mold also includes a second side for mating with the first side to close a mold cavity around the outlet end of the syringe body when inserted therein.

The syringe is manufactured using a standard syringe and overmolding a tip on the pre-molded syringe body, thereby providing a bonded tip on the syringe body. The tip is suitably sized and shaped for enteral-only connection. Thus, a tip is added to form an enteral-only syringe. The overmolding permits use of a different tip colour, such as orange, for identification of the syringe as an enteral-only syringe while the remainder of the body has a desirable clear or natural colour for viewing the contents of the syringe. Further, the overmolded tip inhibits connection to a non-enteral connector, thereby reducing the chance of mistakenly delivering enteral feeding fluid to, for example, an intravenous line. Use of a cavity block within the mold for overmolding the tip provides a smooth tip end. Thus, no line is left at the end of the tip where the two mold halves meet, which allows for a better seal when connecting to an enteral connector at an enteral feeding line or enteral extension set.

BRIEF DESCRIPTION OF THE DRAWINGS

The present invention will be better understood with reference to the drawings and to the following description in which:

FIG. 2 is a perspective view of a portion of a mold for injection molding an enteral tip on a syringe and showing a standard syringe for insertion into the open mold, according to an embodiment;

FIG. 3 is a perspective view of a portion of the mold of FIG. 2 drawn to a larger scale and showing a portion of a cavity block cut away;

DETAILED DESCRIPTION OF THE PREFERRED EMBODIMENTS

Figure 1:
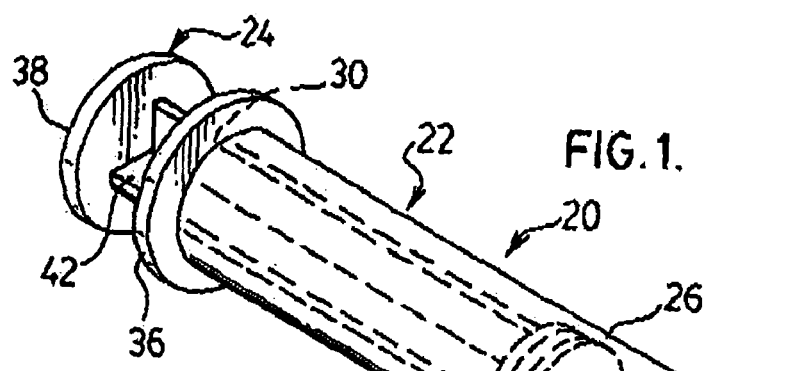
FIG. 1 is a perspective view of a standard syringe.

Reference is first made to FIG. 1 to describe a syringe for use in manufacturing an enteral-feeding syringe and indicated generally by the numeral 20. The syringe shown in FIG. 1 is referred to herein as the premolded syringe 20 as the parts, including the body, are premolded and preassembled. The premolded syringe 20 includes a syringe body 22 and a plunger 24 for insertion into the syringe body 22. The syringe body 22 is a generally hollow, tubular barrel 26 extending between a tapered end wall 28 and an open plunger end 30 into which the plunger 24 is inserted, thereby defining a reservoir for receiving fluid. A tip 32 extends from the end wall 28 and defines an outlet end 34 that is in fluid connection with the reservoir for delivery of the fluid from the reservoir. The open plunger end 30 of the body 22 includes a flange 36 extending radially outwardly from the exterior of the barrel 26.

The plunger 24 includes an exterior end 38 for depressing with the thumb to express the contents in the reservoir and an interior end 40 for mating with the interior of the tubular barrel 26 to form a seal for pushing the contents from the reservoir and through the tip 32 when the exterior end 38 is depressed. A generally X-shaped cross-sectional shank 42 extends between the exterior end 38 and the interior end 40. An O-ring 44 is seated in a groove around the circumference of the interior end 40 to aid in forming the seal with the interior of the tubular barrel 26.

Reference is now made to FIGS. 2 to 5 to describe a mold 50 that is used for overmolding in manufacturing an enteral-feeding syringe. The mold 50 includes a first side 52 and a second side 54 that mate together to form the mold cavity. The first side 52 has a slot 56 that is sized and shaped to receive the premolded syringe 20 therein. Similarly, the second side 54 has a slot 58 that is sized and shaped to receive the premolded syringe 20 therein and to mate with the first side 54 during molding. Each of the slots 56, 58, includes a respective recess 60, 62 for receiving the flange 36 of the premolded body, and a respective semi-circular edge 64, 66 located proximal the end wall 28 of the premolded syringe 20 during molding. Each slot 56 also includes a respective tip seat 68, 69 adjacent the semi-circular edge 64, 66. The tip seat 68, 69 is sized and shaped to fit a portion of the tip 32 closest to the end wall 28 such that when the mold 50 is closed, the tip seats 68, 69 form a tight fit with a portion of the tip 32 to close off the mold cavity. Each slot also includes respective grooves 70, 71 adjacent the respective tip seats 68, 69 such that the end portion of the tip 32 is located between the grooves 70, 71 and spaced therefrom when the premolded syringe 20 is located in the mold 50 during overmolding. The end of the tip is spaced from the grooves 70, 71, thereby providing a portion of the mold cavity.

The first side 52 of the mold includes an enteral tip cavity block 72 that includes a generally conical cavity for the formation of an enteral tip segment. A core pin 74 extends from a back 76 of the enteral tip cavity block 72, through and concentric with the conical cavity. The core pin 74 has a first cylindrical segment 78 located within the cavity block 72 and a second cylindrical segment 80 of reduced diameter that extends out from the cavity block 72 and is concentric with the groove 70. Thus, a step 82 is provided between the first cylindrical segment 78 and the second cylindrical segment 80 that acts as a stopper. It will be appreciated that the second side 54 of the mold 50 includes a complementary void for receiving the cavity block 72 of the first side 52 of the mold 50 therein.

To load the premolded syringe 20 into the mold 50 for overmolding, the syringe 20 is located in the first side 52 of the mold 50 such that the second cylindrical segment 80 of the core pin 74 is located inside the tip 32. The second cylindrical segment 80 is sized and shaped to closely fit the interior diameter of the tip 32 and the outlet end 34 of the tip 32 abuts the step 82 of the core pin 74, thereby inhibiting the ingress of melted plastic into the tip 32 during molding. When located in the first side 52 of the mold 50, the flange 36 of the premolded syringe 20 is located in the recess 60 and the end wall 28 is proximal the edge 64. The mold 50 is then closed by mating the first side 52 and second side 54 together. The premolded syringe 20 is retained with the flange 36 located in the recesses 60, 62 and the end wall 28 proximal the edges 64, 66. The mold cavity is defined within the cavity block 72 and between the grooves 70, 71 for overmolding.

Figure 6:
FIG. 6 is a perspective view of a portion of an enteral syringe according to an embodiment.
Figure 7:
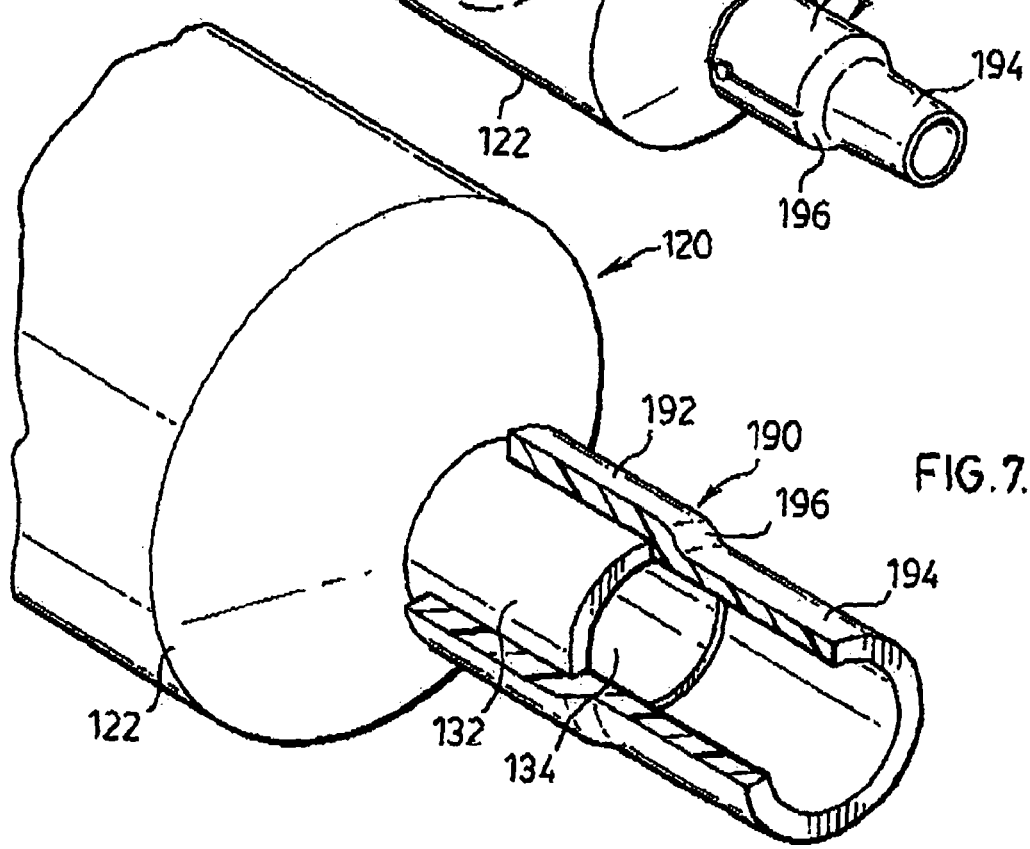
FIG. 7 is a perspective view of a portion of the enteral syringe of FIG. 4, drawn to a larger scale and showing a portion of an enteral tip cut away.
Figure 4:
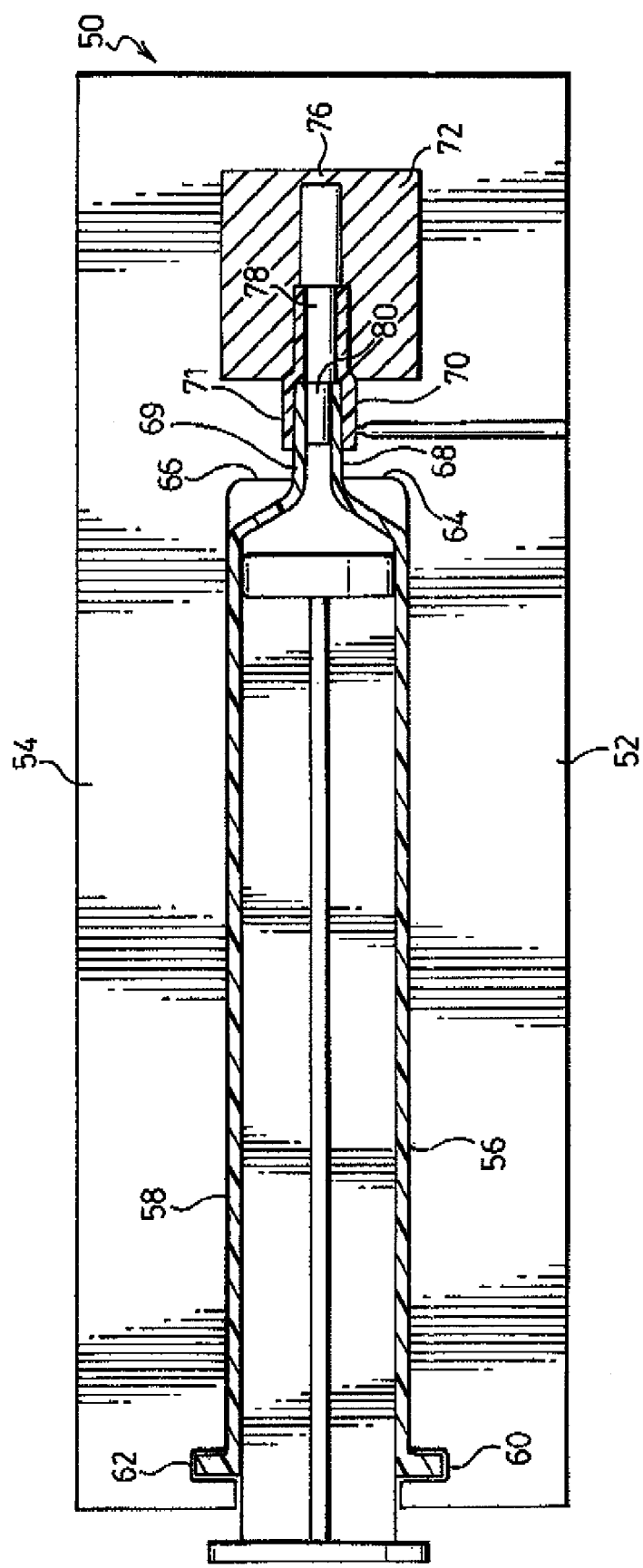
FIG. 4 is a sectional view of the mold in a closed position with an molded enteral tip on a syringe body.

Referring now to FIGS. 6 and 7, there is shown a portion of an enteral syringe for use in enteral feeding according to one embodiment. The numerals used previously in describing the premolded syringe 20 will now be raised by 100 to describe the present embodiment and thus, the enteral syringe of FIG. 4 is indicated generally by the numeral 120. The enteral syringe 120 includes many similar features to that described above with reference to FIG. 1. The enteral syringe, however, includes an enteral tip 190 that is overmolded on the outlet end 134 of the syringe body 122 and sized for insertion into an enteral connector.

Figure 5:
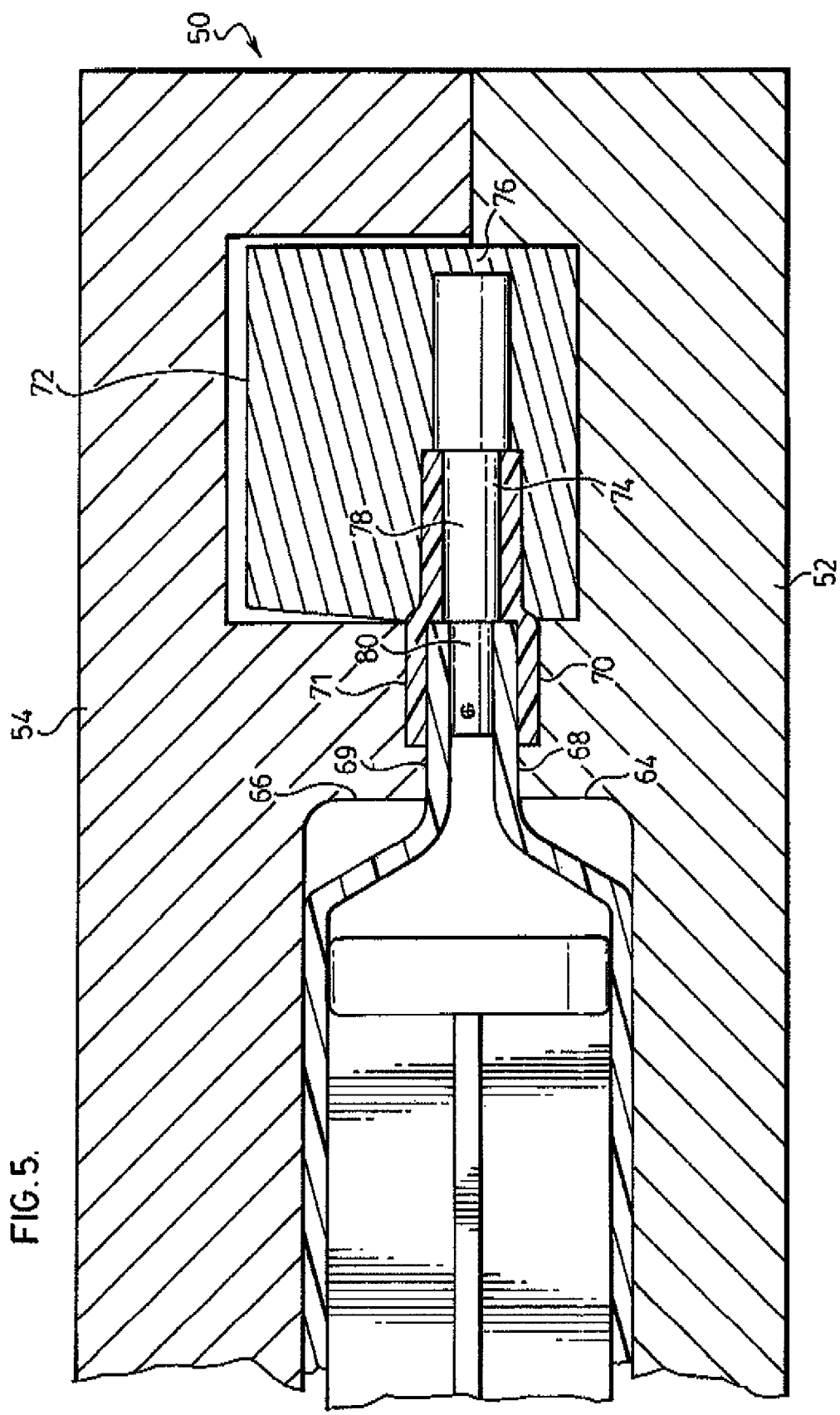
FIG. 5 is a partial sectional view of the mold and the molded enteral tip on the syringe body of FIG. 6, drawn to a larger scale.

The enteral tip 190 includes a cover portion 192 that overlaps with and covers the tip 132, as best shown in the cut-away view of FIG. 5, and an extension portion 194 that extends axially from the tip 132. A step 196 is formed in the enteral tip 190, between the cover portion 192 and the extension portion 194. The extension portion 194 is sized for enteral-only use. The extension portion 194 is approximately 0.287 inches (~7.29 mm) in length and is tapered from a diameter of about 0.193 inches (~4.902 mm) adjacent the step 194 to about 0.183 inches (~4.648 mm) at the end for enteral-only use. As shown, the enteral tip 190 is concentric with the tip 132 and provides a passageway in fluid communication with the tip 132 and thus, with the reservoir. The enteral tip 190 is bonded to the tip 132 by overmolding.

A method of manufacturing the enteral syringe 120 for use in enteral feeding will now be described with reference to the Figures.

The premolded syringe 20 is first loaded into the open mold 50 for overmolding. As described above, the second cylindrical segment 80 of the core pin 74 is located in the tip 32 of the premolded syringe 20 and the outlet end 34 of the tip 32 abuts the step 82 of the core pin 74. The flange 36 of the premolded syringe 20 is located in the recess 60 and the end wall 28 is proximal the edge 64.

Next, the mold 50 is closed by mating the first side 52 and second side 54 together, as best shown in FIGS. 4 and 5. As described above, the premolded syringe 20 is retained with the flange 36 located in the recesses 60, 62 and the end wall 28 proximal the edges 64, 66. Movement of the premolded syringe 20 within the mold 50 is thereby inhibited. Thus, the premolded syringe 20 is inhibited from sliding away from the cavity block 72 when plastic melt is introduced into the mold cavity at high pressure as the flange 36 is located in the recesses 60, 62.

Molding then proceeds with the injection of plastic melt into the mold cavity that is defined by cavity block 72 and between the grooves 70, 71 for overmolding. The plastic used for injection molding can be any suitable plastic that is compatible with the material of the premolded syringe body 22 for bonding therewith during injection molding.

The mold 50 is then cooled, followed by opening of the mold and removal of the enteral syringe 120 including the enteral tip 190.

It will be appreciated that the extension portion 194 of the enteral tip 190 is formed inside the enteral tip cavity block 72 while the cover portion 192 of the enteral tip 190 is formed within the portion of the mold cavity defined by the grooves 70, 71, outside the cavity block 72. The extension portion 194 is therefore free of a parting line formed where two mold parts meet. Thus, there is no parting line on the extension portion 194 that interferes with the operation of the enteral tip 190.

While the embodiments described herein are directed to particular implementations of the present invention, it will be understood that modifications and variations to these embodiments are within the scope and sphere of the present application. For example, the size and shape of many of the features of the above-described embodiments can vary while still performing the same function. The flange described above, for example, can be a pair of grip wings. Also, it is possible that only the premolded syringe body is placed in the mold during overmolding, rather than the syringe and the plunger. Many other modifications and variations may occur to those skilled in the art. All such modifications and variations are believed to be within the sphere and scope of the present application.

The invention claimed is:

1. A method of manufacturing a syringe for use in enteral feeding, the method comprising:
   providing a premolded syringe body having a plunger end and a forwardly projecting outlet end;
   loading the premolded syringe body into a mold having a core pin extending from an internal cavity block and into the outlet end of the premolded syringe body, the cavity block having a cavity in the shape of a tip located adjacent the outlet end of the premolded syringe body for forming an enteral tip free of a mold parting line therein;
   closing the mold to retain the premolded syringe body and internal cavity block therein;
   injection molding by injecting plastic molding material into the mold cavity, and cooling the plastic molding material for simultaneously forming a tip free of a mold parting line in the tip cavity located around the core pin and the outlet end, simultaneously bonding the tip to the outlet end of the premolded syringe body; and
   opening the mold and extracting the premolded syringe body with the tip bonded thereto.

2. The method according to claim 1, wherein loading the premolded syringe body comprises inserting the outlet end to abut a stopper on the core pin.

3. The method according to claim 1, wherein loading the premolded syringe body comprises inserting a gripping flange of the premolded syringe body into a recess in the mold for inhibiting axial movement of the syringe body away from the mold cavity.

4. The method according to claim 1, wherein providing the premolded syringe body comprises providing the premolded syringe body along with a plunger inserted therein and loading the premolded syringe body comprises loading the plunger and premolded syringe body into the mold.

5. A method of manufacturing a syringe for use in enteral feeding, the method comprising:
   providing a premolded syringe body having a plunger end and a forwardly projecting outlet end;
   loading the premolded syringe body into a mold having a core pin extending from an internal cavity block and into the outlet end of the premolded syringe body, the internal cavity block having a cavity in the shape of a tip located adjacent the outlet end of the premolded syringe body for forming an enteral tip free of a mold parting line therein, the mold having a groove provided around the outlet end of the premolded syringe body;
   closing the mold to retain the premolded syringe body and internal cavity block therein;
   injection molding by injecting plastic molding material into the mold cavity for filling the tip cavity and groove, and cooling the plastic molding material for simultaneously forming a tip free of a mold parting line in the tip cavity located around the core pin and a cover in the groove surrounding the outlet end, simultaneously bonding the tip to the outlet end of the premolded syringe body; and
   opening the mold and extracting the premolded syringe body with the tip bonded thereto.

\* \* \* \* \*